(12) United States Patent  
Socha et al.

(10) Patent No.: US 8,107,080 B2  
(45) Date of Patent: Jan. 31, 2012

(54) ENVIRONMENTAL CONTROL OF FLUID SAMPLES, CALIBRATION, AND DETECTION OF CONCENTRATION LEVELS

(75) Inventors: Jeffrey Socha, Boylston, MA (US); Dieter Kita, Blackstone, MA (US); Robert D. Bailey, Bellingham, MA (US); Yongquan Li, Schenectady, NY (US)

(73) Assignee: Thermo Fisher Scientific Inc., Waltham, MA (US)

( * ) Notice: Subject to any disclaimer, the term of this patent is extended or adjusted under 35 U.S.C. 154(b) by 318 days.

(21) Appl. No.: 12/463,915

(22) Filed: May 11, 2009

(65) Prior Publication Data

US 2010/0284006 A1    Nov. 11, 2010

(51) Int. Cl.  
*G01N 21/00* (2006.01)
(52) U.S. Cl. .................. 356/436; 356/437; 356/438
(58) Field of Classification Search .......... 356/436–445  
See application file for complete search history.

(56) References Cited

U.S. PATENT DOCUMENTS

| 3,749,495 A | 7/1973 | Wilkins et al. |
| 5,178,022 A | 1/1993 | Tomlin |
| 5,709,082 A | 1/1998 | Harris et al. |
| 2005/0241416 A1* | 11/2005 | DeFriez et al. ............ 73/863.12 |

OTHER PUBLICATIONS

International Search Report, Jun. 29, 2010, pp. 2.

* cited by examiner

*Primary Examiner* — Michael P Stafira  
(74) *Attorney, Agent, or Firm* — Chapin IP Law, LLC; Barry W. Chapin (57) ABSTRACT

According to example configurations herein, a system includes an inertial filter, a temperature controller, and analyzer. The inertial filter has multiple ports including a first port, a second port, and a third port. A sample gas flows between the first port and the third port of the inertial filter. The second port of the inertial filter outputs a portion of the gas flowing between the first port and the second port. The temperature controller controls a temperature of the inertial filter and/or the gas flowing through the inertial filter. The analyzer receives the portion of the gas flow outputted by the second port of the inertial filter and produces a value indicative of a concentration of sulfur trioxide in the portion of the gas flow.

20 Claims, 9 Drawing Sheets

ENVIRONMENTAL CONTROL OF FLUID SAMPLES, CALIBRATION, AND DETECTION OF CONCENTRATION LEVELS

RELATED APPLICATIONS

This application is related to U.S. patent application entitled "GENERATION OF SULFUR TRIOXIDE AND SULFURIC ACID," identified as Ser. No. 12/463,795, filed on the same day as the subject application, the entire teachings of which are incorporated herein by this reference.

BACKGROUND

Emissions from fossil fuel combustion facilities, such as flue gases of coal-fired utilities and municipal solid waste incinerators, typically include multiple types of gases. For example, emissions from a smokestack can include gases such as $CO_2$, $NO_2$, $SO_2$, etc.

Many countries regulate emissions of the different types of waste gases because of potential environmental hazards posed by such harmful emissions. Accordingly, many facilities that generate or potentially generate harmful gas emissions need to employ multiple gas analyzer systems to ensure that emitted gases are compliant with corresponding regulations.

In certain cases, there are no particular regulations of certain types of emissions. In such instances, a flue operator may monitor different levels of constituents in a flue output for purposes of controlling a process. Thus, many applications for measuring contaminants such as SO3 and or H2SO4 are more for process control than for compliance emissions monitoring. To detect a presence of the many types of gases, a facility may need to operate multiple independent conventional gas analyzer systems and/or measurement benches. For example, a facility may need to operate a first gas analyzer system to detect a first type of gas, a second analyzer system to detect a second type of gas, and so on. Such instruments may combine multiple complex analytical technologies including electrochemical cells, chemi-luminescence spectroscopy, flame ionization and GFC (Gas Filter Correlation), NDIR (Non-Dispersive Infrared), UV (Ultra-Violet) Spectroscopy, etc., into a single gas analyzer unit to detect one or more types of gases.

Each of the different types of gases emitted by a smokestack has unique absorption characteristics. For example, each gas type can absorb different optical frequencies. The unique absorption characteristics enable a corresponding gas analyzer system to identify whether a particular type of gas is present in a gas sample.

A facility may need to operate multiple independent conventional gas analyzer systems and/or measurement benches to detect a presence of multiple gases of interest. Each conventional gas analyzer system typically requires its own set of operating procedures, calibration procedures, etc., to collect and generate accurate data.

One way to identify a type of gas present in an unknown gas sample is the application of Beer's law. In general, Beer's law defines an empirical relationship that relates the absorption of light to properties of the material through which the light is traveling. In other words, as mentioned above, different materials absorb different frequencies of light energy. Based on detecting which frequencies of optical energy are absorbed by the gas sample, it is possible to determine what type of gas is present in the gas sample. The amount of absorption by a sample can indicate a concentration of a respective gas.

Emissions of sulfur trioxide and/or sulfuric acid from a smokestack into the air may be undesirable for several reasons. Sulfur trioxide and/or sulfuric acid exiting a stack or chimney can add to air pollution. Sulfuric acid is a common agent in acid rain.

Also, sulfur trioxide can be very corrosive to equipment used in combustion facilities thus causing possible damage. Sulfur trioxide exiting a stack can appear as a blue plume, that is, exhaust smoke having a blue color adding to opacity and visual air pollution.

Selective catalytic reduction processes used to reduce other pollutants have created higher sulfur trioxide levels in flue gases. Such higher levels of sulfur trioxide have adversely affected removal of certain pollutants. For example, mercury is commonly removed from flue gases using activated carbon as part of an adsorption process. With higher levels of sulfur trioxide present during the adsorption process, the percent of mercury removed from flue gases dramatically decreases. Because of the potential environmental pollution and other negative effects, it may be useful to measure, monitor, and/or control sulfur trioxide emissions.

Conventional systems for analyzing a presence of sulfur trioxide can suffer from a number of deficiencies. For example, there are several types of detection systems that can be used to measure sulfur trioxide. Such systems include Fourier transform infrared (FTIR) spectroscopy, tunable diode laser spectroscopy, acid dew-point, conversion/fluorescence, filter correlation, and cavity ring-down systems. The current state of the art for measuring $SO_3/H_2SO_4$ in flue gas is a wet chemistry approach referred to as Control Condensate, where a sample is extracted, the cooled $SO_3$ in the presence of water forms $H_2SO_4$, which is collected and then chemically analyzed in a lab

BRIEF DESCRIPTION

Some of the conventional systems as mentioned above measure sulfur trioxide directly, while others measure sulfur trioxide indirectly. For example, an acid dew-point system measures sulfuric acid, and the results can be used to infer sulfur trioxide amounts. More specifically, the acid dew point system infers $H_2SO_4$. For example, it only detects an acid dewpoint, which in conjunction with a water concentration and gas temperature information, can be used to calculate $H_2SO_4$. A conversion/fluorescence system requires conversion of sulfur trioxide to sulfur dioxide. In such a system, the measurement of sulfur dioxide is used to infer sulfur trioxide amounts. Some of these systems have a poor detection limit, meaning that some systems cannot measure sulfur trioxide amounts below a certain concentration or relative proportion of flue gases.

One relevant inaccuracy to appreciate is that the chemical industry, by and large, labels both $H_2SO_4$ and $SO_3$ with the term sulfur trioxide. In most conventional applications, distinguishing between the two compounds is not important, and so this inaccurate identification exists in conventional discussions. This means that there are cases of systems that claim to measure sulfur trioxide, when in reality this is not a direct measurement. Such systems indirectly measure sulfur trioxide and then infer or calculate what sulfur trioxide amounts existed before conversion or condensation to sulfuric acid. Conventional systems perform in this manner because it can be difficult to prevent sulfur trioxide from converting into sulfuric acid. As mentioned above, conventional systems typically measure a concentration of sulfuric acid, which is then used to infer a concentration of sulfur trioxide in a sample.

Embodiments herein deviate with respect to conventional analyzer systems. For example, at least some embodiments herein are directed to one or more unique ways of implementing a chemical analyzer. The analyzer can be configured to control environmental parameters of a fluid sample and detect concentrations of a constituent such as sulfur trioxide in a fluid sample.

More specifically, one embodiment herein includes an inertial filter, a temperature controller, and analyzer. The inertial filter has multiple ports including a first port, a second port, and a third port. The second port of the inertial filter outputs a portion of a gas flowing between the first port and the third. The temperature controller controls a temperature of the gas flowing through the inertial filter from the first port to third port or from the third port to the first port. The analyzer receives the portion of the gas flow outputted from the second port of the inertial filter and produces a value indicative of a concentration of sulfur trioxide in the portion of the gas flow.

In an example embodiment, the temperature controller heats the inertial filter to prevent conversion of sulfur trioxide (i.e., $SO_3$) in the passing gas from converting into sulfuric acid ($H_2SO_4$). Accordingly, embodiments herein enable passing of a sample gas having an unknown amount of sulfur trioxide through a heated inertial filter.

In accordance with further embodiments, the temperature controller controls the inertial filter and/or gas therein to a temperature in a range between 250 and 450 degrees Celsius to prevent conversion of sulfur trioxide in the portion of the gas from converting into sulfuric acid.

The system herein can include an optical cavity through which to pass a sample gas received from the second port of the inertial filter. In such an embodiment, the analyzer detects a concentration of sulfur trioxide in the sample gas received from the second port based on an amount of optical absorption by the sample gas in the optical cavity. To prevent conversion of the sulfur trioxide in the sample gas to sulfuric acid, embodiments herein can include heating the optical cavity and/or gas therein to a temperature in a range between 250 and 450 degrees Celsius.

Yet further embodiments herein can include environmental control mechanisms to provide more accurate concentration readings. For example, the system as described herein can include a dilution module and/or one or more pressure reducer stages along a flow path. By way of a non-limiting example, the one or more pressure reducers can be one or more corresponding orifices.

When used, the dilution module produces a diluted sample gas based on dilution of the portion of gas received from the second port of the inertial filter. In other words, the dilution module receives the gas sample outputted by the second port of the inertial filter and then mixes the received gas sample with a dilution gas such as air, nitrogen, etc. As will be discussed, subsequent to dilution, the analyzer detects a concentration of sulfur trioxide in the diluted sample gas based on an amount of optical absorption by the diluted sample gas.

As mentioned, a system according to embodiments herein can include a pressure reducer to reduce a pressure of the sample gas received from the second port of the inertial filter prior to dilution of the sample gas by the dilution module. More specifically, a pressure reducer can be positioned in a flow path between the second port of the inertial filter and the dilution module to reduce a pressure of the gas sample prior to receipt of the gas sample at the dilution module. Reducing a pressure of the gas sample and diluting the gas sample reduces a possibility of undesirable chemical reactions in the gas sample being conveyed to the analyzer.

Embodiments herein can include an additional pressure reducer stage in a path in which the gas sample is conveyed to an optical cavity associated with the analyzer. For example, a pressure of the diluted gas sample produced or outputted by the dilution module can be reduced as well. Thus, a pressure of the diluted gas sample passing through the optical cavity can be of a lower pressure than a pressure of the diluted gas sample outputted by the dilution module. This pressure reduction stage (after the dilution module) reduces a possibility that the sulfur trioxide in the sample will convert into sulfuric acid.

As previously discussed, a heater can be configured to heat the optical cavity to prevent conversion of sulfur trioxide in the diluted sample gas into sulfuric acid.

In accordance with yet further embodiments, the gas analyzer system can include a first conduit and a second conduit. During a first time duration, the first conduit conveys a first sample gas to the first port of the inertial filter such that the first sample gas flows from the first port to the third port of the inertial filter. The first sample gas can be provided by a source such as a flue or smokestack. In such an embodiment, the first sample gas received from the second port of the inertial filter has an unknown concentration of sulfur trioxide and is optically analyzed (in a manner as discussed above) to determine a respective concentration of the sulfur trioxide.

During a second time duration, the second conduit conveys a second sample gas to the third port of the inertial filter such that the second sample gas flows from the third port through the inertial filter out the first port of the inertial filter. A portion of the second sample gas passing through the inertial filter is outputted from the second port of the inertial filter. The second sample gas can have a known concentration of sulfur trioxide for calibrating the analyzer as discussed above. Accordingly, the first sample gas can be passed in one direction through the inertial filter and, at a different time, the second sample gas can be passed in an opposite direction through the inertial filter.

These and other more specific embodiments are disclosed in more detail below.

It is to be understood that the system, method, apparatus, etc., as discussed herein can be embodied strictly as hardware, as a hybrid of software and hardware, or as software alone such as within a processor, or within an operating system or a within a software application.

As discussed above, techniques herein are well suited for use in chemical analyzer systems. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where appropriate, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION

One embodiment herein includes an inertial filter, a temperature controller, and an analyzer. The inertial filter has multiple ports including a first port, a second port, and a third port. A sample gas flows between the first port and the third port of the inertial filter. For example, a gas sample can enter the first port, flow through the inertial filter, and exit from the third port of the inertial filter. Also, a gas sample can enter the third port, flow through the inertial filter, and exit from the first port of the inertial filter. The second port of the inertial filter outputs a portion of the gas flowing between the first port and the second port. The temperature controller controls a temperature of the inertial filter and/or the gas flowing through the inertial filter to deter the gas (or components therein) in the inertial filter from converting into an undesirable state. The analyzer receives the portion of the gas flow outputted by the second port of the inertial filter and produces a value indicative of a concentration of a contaminant such as sulfur trioxide in the portion of the gas flow.

In general, as described herein, an inertial filter style probe, operating at an elevated temperature (e.g., 250-450 degree Celcius) is used to extract a particulate free gas sample containing $SO_3$ and/or $H_2SO_4$ from a combustion effluent. The probe can include a dilution module, which is used to dilute the sample in order to ease in the transport of this reactive sample. A measurement cell may also be coupled to this probe (or even within this probe) in order to eliminate/reduce transport issues. Any sample transport can be done under reduced pressure in order to limit the reaction which would bias the measurement of $SO_3$/H2SO4.

Since the sample may be a mix of both $SO_3$ and $H_2SO_4$ (this is a function of temperature, pressure, and moisture content) depending upon the extraction location, embodiments herein can be operated at either an elevated temperature to drive the $H_2SO_4$ into mostly (or nearly all) $SO_3$, or conversely decreased in temperature to drive the $SO_3$ into mostly (or nearly all) $H_2SO_4$. The advantage of doing this is so that a single detection approach can be used to measure $SO_3$ or $H_2SO_4$, depending on the requirement. For example, an optical analysis can be performed on the sample gas to determine an amount of sulfur trioxide or an amount of sulfuric acid. A catalyst/converter can be employed in order to fully drive a reaction either into substantially all sulfur trioxide or substantially all sulfuric acid. Thus, the analyzer and corresponding optical measurement system as described herein can be configured to detect an amount of sulfur trioxide in a gas sample or an amount of sulfuric acid in a respective gas sample.

Figure 1:
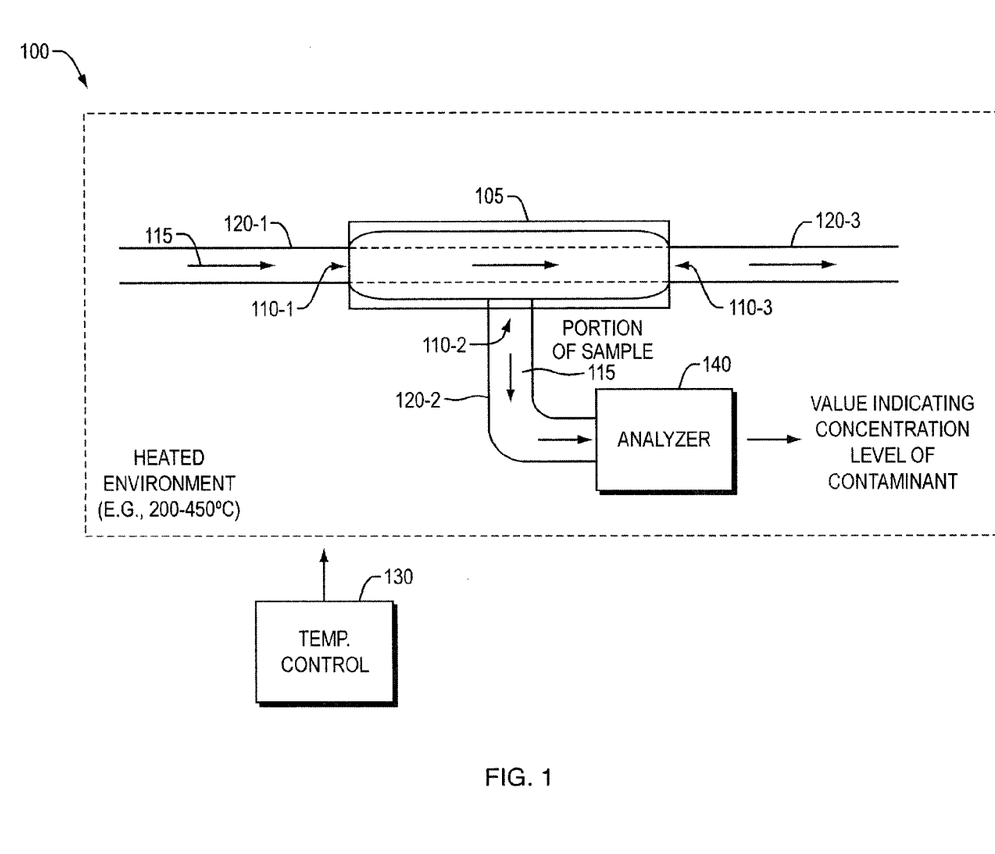
FIG. 1 is an example diagram of a system for analyzing one or more gas samples according to embodiments herein.

FIG. 1 is an example diagram of a system for analyzing one or more gas samples according to embodiments herein. As shown, system 100 includes an inertial filter 105 having multiple ports 110. Specifically, the multiple ports 110 include port 110-1, port 110-2, and port 110-3. Port 110-1 and port 110-3 reside at axial ends of the inertial filter 10-5. Port 110-2 forms a "T" type of output for outputting gas flowing along an axis of the inertial filter 105. Conduits 120 such as conduit 120-1, conduit 120-2, and conduit 120-3 convey sample gas 115 throughout system 100 as shown.

More specifically, conduit 120-1 conveys sample gas 115 from a source such as a flue to port 110-1 of the inertial filter 105. The sample gas 115 passes through a hollow core of the inertial filter 105 and exits at port 110-3. Typically, most of the gas sample 115 entering port 110-1 is outputted at port 110-3 to conduit 120-3. A portion of the gas sample 115 is outputted from port 110-2 of the inertial filter 105.

A speed of the gas sample flowing through the inertial filter 105 can be high enough to prevent particulates in the gas sample from passing through port 110-2. For example, in one embodiment, the sample gas 115 can include undesirable particulates that can clog conduits and/or other paths through system 100. Inertial filter 105 substantially reduces or eliminates an amount of the particulates that would otherwise pass through port 110-2 inertial filter the inertial filter 105 were simply a T-shaped connection without a core filter therein. According to embodiments herein, the sample gas 115 passes through the inertial filter 105 at a sufficient velocity such as 50-100 feet per second such that any or most particulates (e.g., solids) in the gas sample 115 pass through the inertial filter 105 to port 110-3. As mentioned, port 110-2 outputs a portion of the sample gas 115 flowing through the inertial filter 105. The portion of the gas sample 115 exhausted from port 110-2 of the inertial filter 105 has a low amount of particulates and thus does not a flow path towards analyzer 140.

System 100 can include a temperature controller 130. In one embodiment, the temperature controller 130 maintains a temperature of the inertial filter 105 to a temperature in a range between 200 and 600 degrees Celsius. Maintaining the temperature of the inertial filter 105 and surrounding environment at such a hot temperature reduces an amount of sulfur trioxide in the gas sample 115 from converting into sulfuric acid. When the temperature controller 130 maintains the temperature to greater than 300 degrees Celsius, a relatively low amount (if any) of sulfur trioxide in the gas sample 115 changes into sulfuric acid.

Referring again to the flow of the sample gas outputted from port 110-2 of the inertial filter 105, conduit 120-2 conveys the outputted portion of the gas sample 115 (which is relatively free of particulates due to the inertial filter 105) to analyzer 140. As its name suggests, and as will be discussed further in this specification, analyzer 140 analyzes the received gas sample 115 and generates an output value 150 indicative of a concentration of sulfur trioxide in the gas sample 115.

Sample Collection Mode

Figure 2:
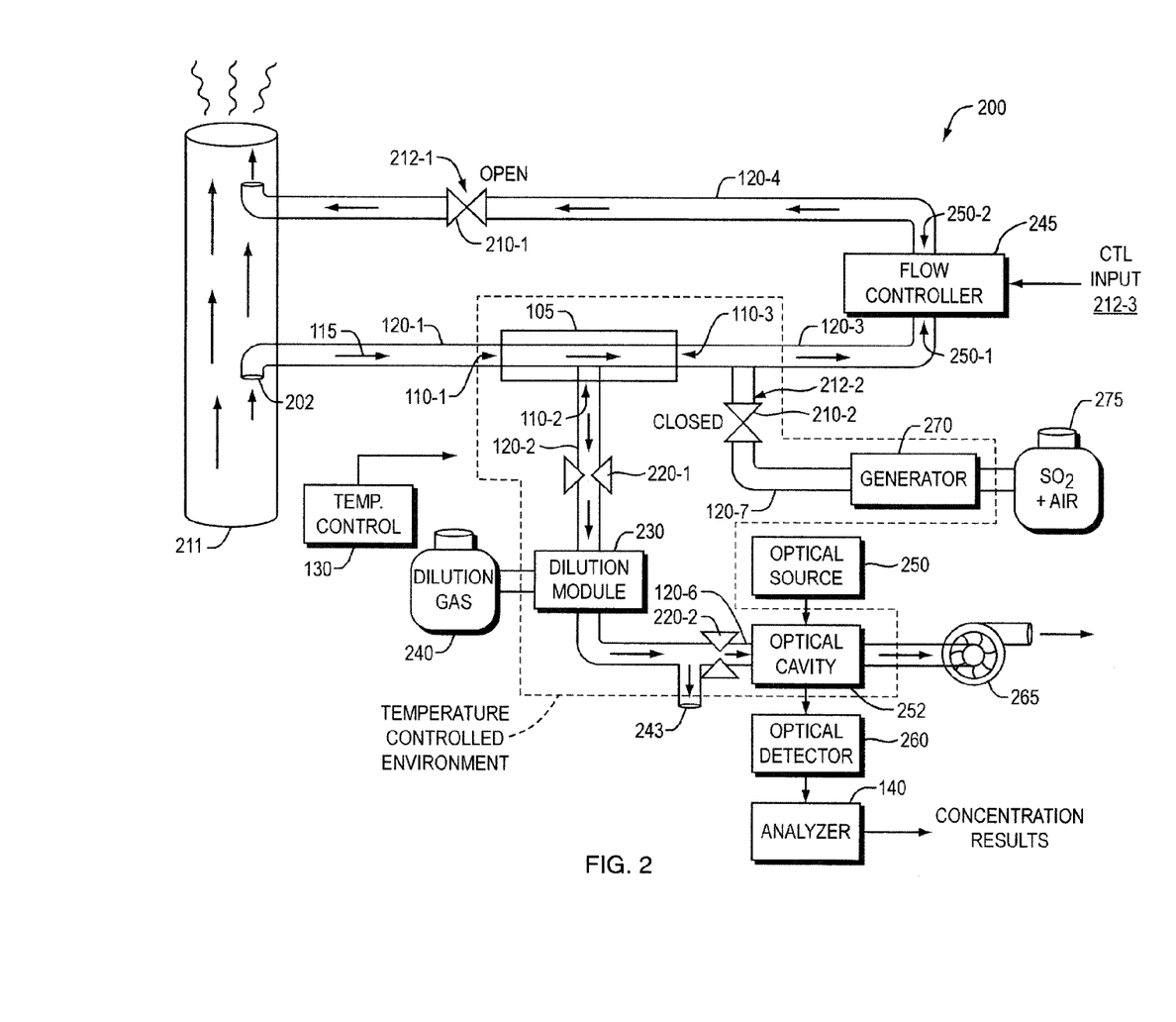
FIG. 2 is a detailed example diagram of a system for analyzing one or more gas samples having unknown concentrations of contaminants according to embodiments herein.

FIG. 2 is a more detailed example diagram of a system 200 for analyzing one or more gas samples according to embodiments herein. As shown, system 200 includes a collector port 202 disposed in flue 211 (e.g., smokestack). The collector port 202 captures a gas sample 115 from the flue 211. As mentioned, the gas sample 115 collected from flue 211 can have an unknown concentration of sulfur trioxide.

In one embodiment, the gas sample 115 is sucked or drawn from the flue 211 along the multiple paths as highlighted by respective arrows. For example, while valve 210-1 is set to an OPEN position and valve 210-2 is set to a closed position, the flow controller 245 draws the gas sample 115 from the flue 211 through a combination of conduit 120-1, inertial filter 105, and conduit 120-3. Flow controller 245 outputs the gas sample 115 back to a destination such as the flue 211.

In one embodiment, the flow controller 245 is an eductor device configured to draw the gas sample from the flue 211. Application of a control input 212-3 such as a high-pressure fluid into the flow controller 245 causes a draw of the gas sample 115 into port 250-1 of the flow controller 245. The gas sample 115 is outputted from port 250-2 of the flow controller 245 along with the high-pressure fluid inputted into the flow controller 245. Accordingly, the flow controller 245 facilitates drawing of the gas sample 115 through the inertial filter 105 via application of control input 212-3. Other techniques of drawing the gas sample from the flue 202 can be implemented to achieve similar results as just described.

While the flow controller 245 draws the gas sample 115 through the inertial filter 105, a portion of the gas sample 115 passing through the inertial filter 105 is outputted from port 110-2 into conduit 120-2. Conduit 120-2 conveys the gas sample 115 received from port 110-2 to pressure reducer 220-1. In one embodiment, pressure reducer 220-1 is an orifice configured to reduce a pressure of the gas sample 115. The pressure reducer 220-1 can be an orifice of size 0.005" allowing flow such as 250 sccm.

By way of a non-limiting example, the pressure of the gas in conduit 120-2 is approximately atmospheric pressure. The pressure between pressure reducer 220-1 and dilution module 230 can be <½ atmospheric (to maintain a flow through the orifice). The pressure of stream 220-2 can be atmospheric pressure. The pressure between reducer 220-2 and pump 265 can be approximately ¹⁄₂₀ atmospheric pressure.

Conduit 120-5 conveys the reduced pressure gas sample 115 into dilution module 230 as shown. As its name suggests, the dilution module 230 dilutes the gas sample 115 with dilution gas 240 by a factor such as between 3 and 50. In other words, when implementing a dilution factor of 5, the dilution module 230 can mix four parts of dilution gas 240 for every one part of the gas sample 115. When implementing a dilution factor of 30, the dilution module 230 can mix twenty-nine parts of dilution gas 240 for every one part of the gas sample 115. Dilution gas 240 can be a gas such as air, nitrogen, etc. Other dilution factors outside of the range 5-30 can be implemented as well.

In one embodiment, the dilution module 230 is an eductor. In such an embodiment, the conduit 120-5 provides an input to the eductor. Dilution gas 240 is pressurized to a value such as 25 to 50 psig and provides an output flow of gas between one and ten liters/minute.

The dilution module 230 outputs the diluted gas sample 115 (e.g., a mixture of the dilution gas 240 and the gas sample 115) to conduit 120-6.

Reducing the pressure of the gas sample 115 and, thereafter, diluting the gas sample 115 as discussed above is useful to slow down possible reactions in the gas sample 115. In such an embodiment, any amount of sulfur trioxide in the gas sample 115 is less likely to change into sulfuric acid.

System 200 can include optical equipment configured to detect an amount of absorption caused by contaminants such as sulfur trioxide in the gas sample 115. In one embodiment, such optical equipment can include an optical source 250, an optical cavity 252, and optical detector 260.

To calculate a concentration or amount of a contaminant such as sulfur trioxide in the gas sample 115, the system employs an exhaust device 265 to draw a portion of the sample present in conduit 120-6 through the optical cavity 252. By way of a non-limiting example, conduit 120-6 can include an outlet 243 to dump off an excess amount (e.g., 50-99%) of the gas sample in conduit 120-6. This prevents over pressurizing the system. A balance of the (diluted and reduced pressure) gas sample 115 passes at a rate of between 0.05 and 0.5 liters/minute through the optical cavity 252. Via a vacuum provided by the exhaust device 265, the system 200 maintains a pressure of the gas sample 115 flowing in the optical cavity 252 to a value around 5-50 torr. Conduit 120-6 also can be configured to include pressure reducer 220-2 to reduce the pressure of the diluted sample gas that flows though the optical cavity 252 for analysis by the analyzer 140. The pressure reducer 220-2 can be an orifice of size 0.005" allowing flow such as 250 sccm.

By way of a non-limiting example, as the gas sample 115 passes through the optical cavity, optical source 250 such as a tunable light emitting device, laser diode, or other suitable light source generates an optical signal such as an optical beam at a frequency in the mid-infrared range through the optical cavity 252. After passing through the optical cavity 252, the optical detector 260 receives the optical signal generated by the optical source 250. As mentioned, a portion of the original optical signal is absorbed depending on an amount of contaminants in the gas sample 115. The analyzer 140 then uses the sample data generated by the optical detector 260 to produce one or more values indicating a concentration of sulfur trioxide in the gas sample 115.

In one embodiment, the analyzer 140 generates concentration values based on any or all of the following parameters: an amount of the optical signal that is absorbed by the gas sample in the optical cavity 252, an amount of moisture in the gas sample 115, a temperature of the gas sample 115, and/or a pressure of the gas sample 115. System 200 can include a humidity measuring device to determine an amount of water present in the sample.

In one embodiment, the gas sample collected from the flue 211 can include a combination of both sulfur trioxide and sulfuric acid.

When the optical system 250 is implemented with a laser diode, the laser diode may require cooling down to around −60 degrees Celsius and operate in the mid-infrared frequency range.

The optical source 250 can be tuned to generate an optical signal at which sulfur trioxide and/or sulfuric acid absorbs optical energy. Accordingly, the analyzer 140 determines a concentration of the sulfur trioxide depending on how much of the optical signal is absorbed by the sample.

Also, by way of a non-limiting example, note that the optical cavity 252 can be a cavity such as a single path cavity, a multi-path Harriot cell, etc. To reduce an amount of sulfur trioxide in the gas sample that changes to sulfuric acid, the optical cavity 252 can be heated to a temperature of between 250 and 450 degrees Celsius. As shown, any or all of the following components such as conduits 120, pressure reducer 220, dilution module 230, optical cavity 252, etc., in a gas flow path (as indicated by arrows) can be temperature controlled to prevent conversion of sulfur trioxide into sulfuric acid.

Note that optical source 250 can include a chopper filter as discussed in related U.S. patent application entitled "GAS ANALYZER SYSTEM," Ser. No. 12/112,436, filed on Apr. 30, 2008, and related U.S. patent application entitled "ANALYZER SYSTEM AND OPTICAL FILTERING," Ser. No. 12/112,436, filed on Apr. 30, 2008, the entire teachings of both applications being incorporated herein by this reference.

Calibration Mode

Figure 3:
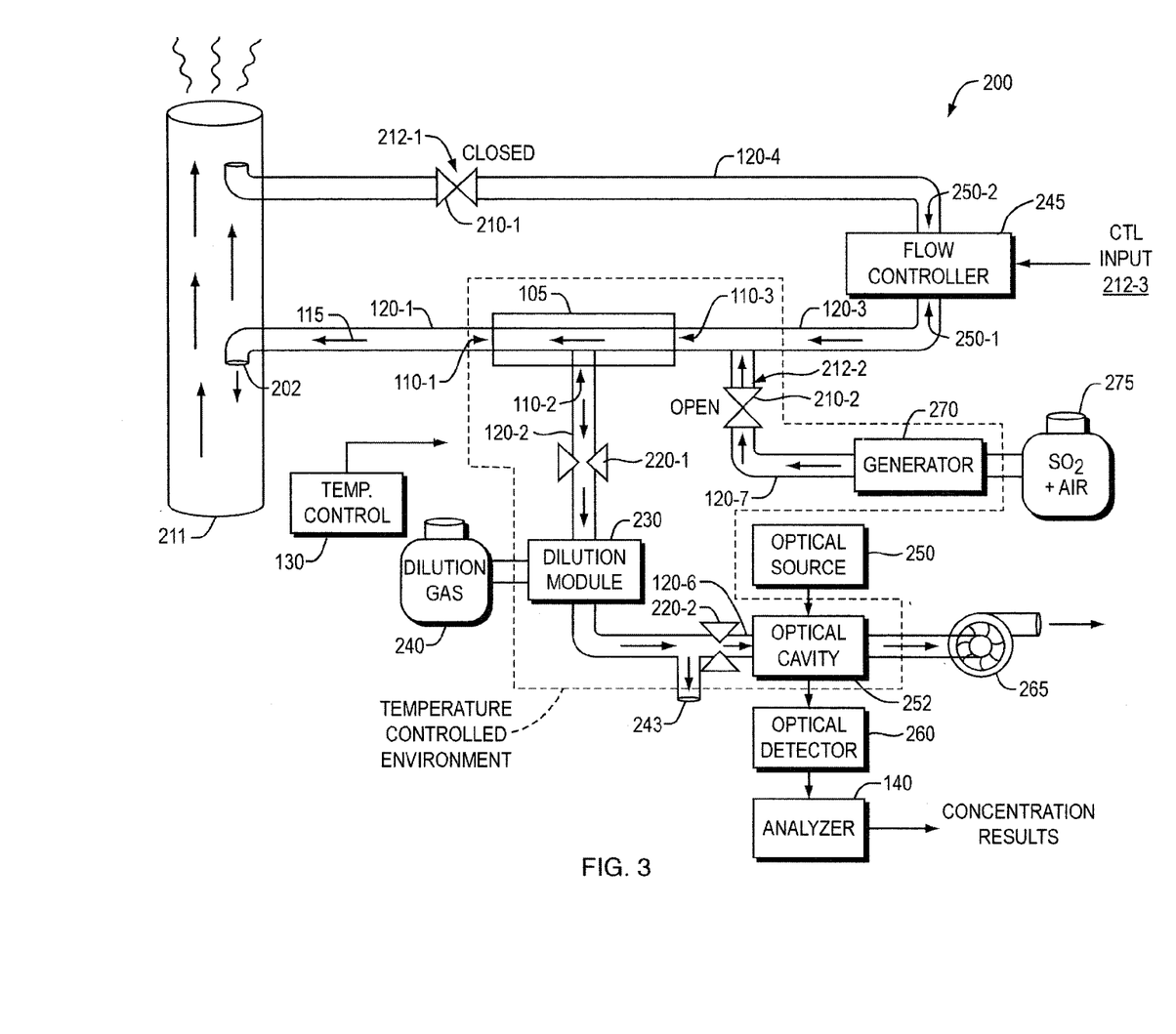
FIG. 3 is a detailed example diagram of a system for analyzing one or more gas samples having known concentrations of a calibration gas according to embodiments herein.

FIG. 3 is an example diagram of a system for analyzing one or more gas samples according to embodiments herein.

The techniques as discussed above in FIG. 2 illustrate how to control environmental conditions so that a gas sample including a contaminant such as sulfur trioxide does not change into sulfuric acid. Additionally, control of environmental parameters (e.g., heating, pressure control, dilution, etc.) along a flow path in system 200 also can facilitate conversion of sulfuric acid in the gas sample 115 into sulfur trioxide. Accordingly, the analyzer 140 can determine an amount of contaminants in the gas sample 115 assuming that most, if not all, of the contaminant in the gas sample 115 is sulfur trioxide rather than sulfuric acid. In this example, the flow controller device (control input 212-3) is turned off, otherwise the motive air for the eductor will also flow backward, diluting the calibration gas.

In a further embodiment such as in a calibration mode, prior to calculating the concentration as mentioned above, embodiments herein include generator 270 for generating a known concentration of sulfur trioxide to calibrate system 200. In the calibration mode as shown in FIG. 3, valve 212-1 is set to a closed position such that the gas in conduit 120-4 does not pass through valve 210-1 to flue 211.

Valve 210-2 is set to an OPEN position. Generator 270 receives a mixture of $SO_2$ and air. Based on the received mixture, the generator 270 converts the mixture into a calibration gas sample having a known concentration of sulfur trioxide. Details of generating the calibration gas sample can be found in co-pending as mentioned above.

During the calibration mode, control input 212-2 sets the valve 210-2 to an open position such that the calibration gas generated by generator 270 passes through the inertial filter 105 in a reverse direction than during the sample collection mode as discussed above for FIG. 2. More specifically, the calibration gas generated by generator 270 flows through conduit 120-3 in the direction as shown, into port 110-3 of inertial filter 105, through inertial filter 105, out port 110-1 of inertial filter 105, and through conduit 120-1 to flue 211. Port 110-2 of inertial filter 105 outputs a portion of the calibration gas sample passing through the inertial filter 105. Conduit 120-2 conveys the portion of calibration sample gas (generated by generator 270) from port 110-2 to the pressure reducer 220 and dilution module 230. In a similar manner as discussed above for the gas sample from flue 211, during the calibration mode, the pressure reducer 220 reduces a pressure of the calibration gas received from port 110-2. The dilution module 230 dilutes the calibration gas sample using a dilution factor of between 3 and 40. The dilution module 230 outputs a diluted calibration gas into conduit 120-6 for subsequent passing of the calibration sample gas through the optical cavity 252 for analysis by analyzer 140. The analyzer 140, in turn, calibrates the optical system (e.g., a combination of optical system 250, optical cavity 252, and optical detector 260) based on an amount of optical energy absorbed by the diluted calibration gas passing through the optical cavity 252.

Figure 4:
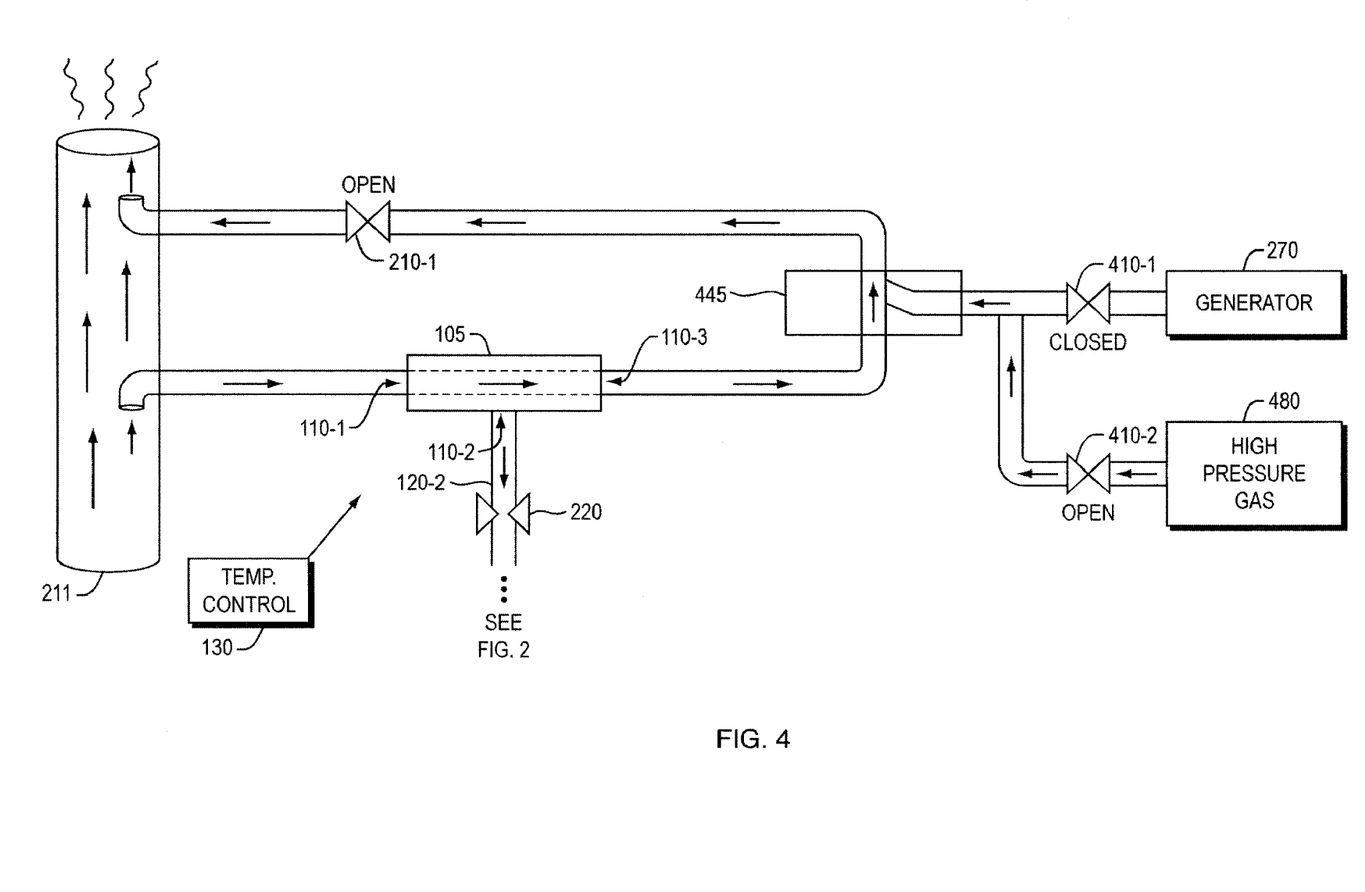
FIG. 4 is an example diagram illustrating a flow of a calibration gas having a known concentration of sulfur trioxide for calibrating an analyzer according to embodiments herein.

FIG. 4 is an example diagram of an analyzer system including an eductor for controlling flow of gases according to embodiments herein. As shown, eductor 445 and settings of corresponding valve 210-1, valve 410-1, and valve 410-2 dictate whether port 110-2 of the inertial filter 105 outputs gas sample 115 or a calibration gas sample to the analyzer 140 and related components.

In this example configuration in which flue gas from flue 211 is tested for a presence of sulfur trioxide, valve 210-1 and valve 410-2 are both set to an OPEN position. Valve 410-1 is set to a CLOSED position. Accordingly, high-pressure gas 480 such as air passes through valve 410-2 into eductor 445. The flow of high-pressure gas 480 into eductor 445 results in drawing of the gas sample 115 through the inertial filter 105. In a manner as previously discussed, a portion of the gas sample 115 passes through port 110-2 of the inertial filter 105 for optical analysis.

Figure 5:
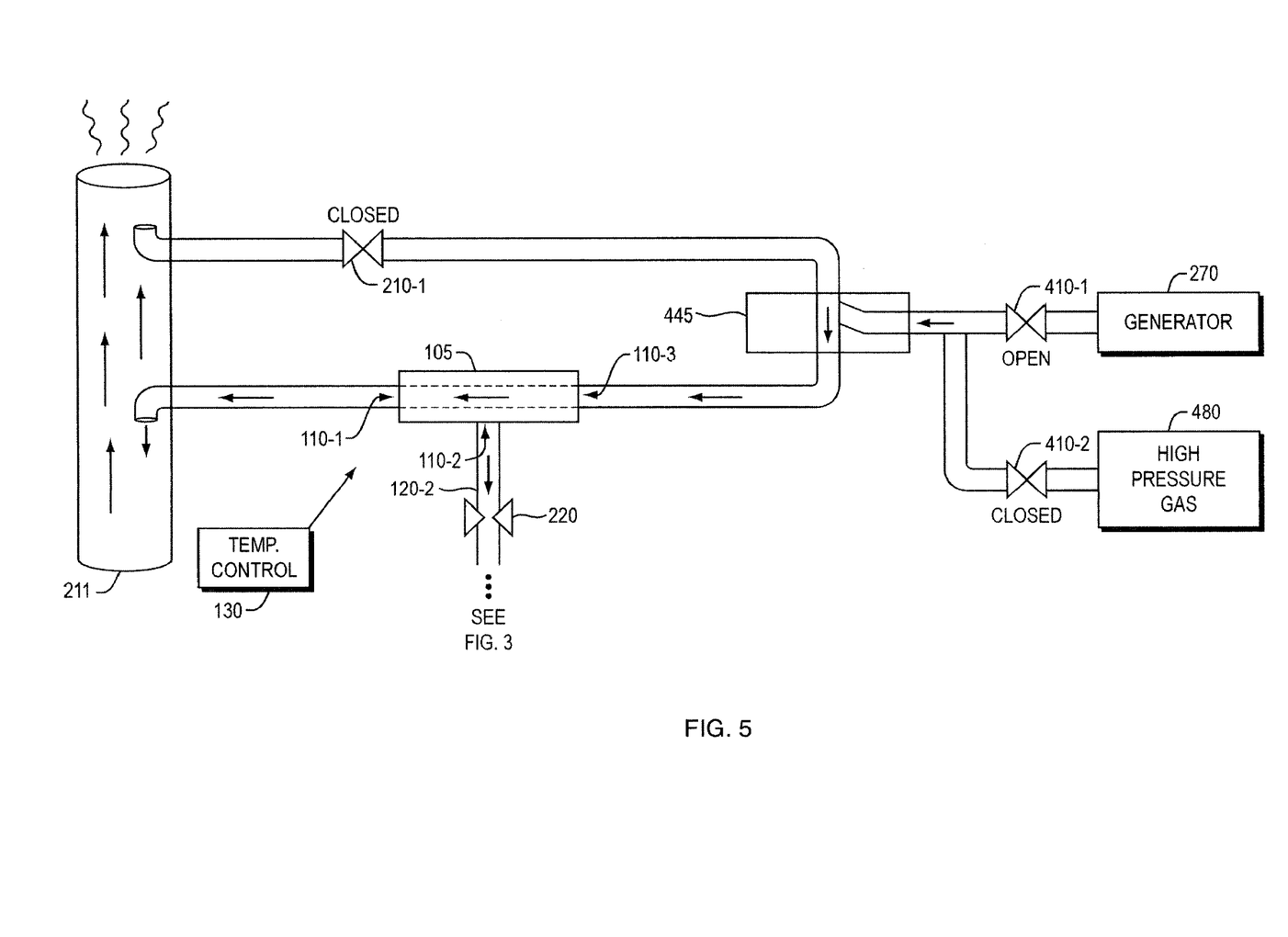
FIG. 5 is an example diagram illustrating a flow of a sample gas having an unknown concentration of sulfur trioxide according to embodiments herein.

FIG. 5 is an example diagram illustrating a flow of a calibration gas having a known concentration of sulfur trioxide for calibrating analyzer 140 according to embodiments herein. As shown, eductor 445 and settings of corresponding valve 210-1, valve 410-1, and valve 410-2 dictate whether port 110-2 of the inertial filter 105 outputs gas sample 115 or a calibration gas sample to the analyzer 140 and related components.

In this example configuration, in which the calibration gas is transmitted to the analyzer 140 for calibration testing, valve 210-1 and valve 410-2 are both set to a CLOSED position. Valve 410-1 is set to an OPEN position. Accordingly, no high-pressure gas 480 such as air passes through valve 410-2 into eductor 445. Instead, generator 270 outputs a calibration gas sample into the eductor 445. Because the valve 210-1 is set to a CLOSED position, the calibration gas flows through the inertial filter 105 in a direction as shown. A portion of the calibration gas sample produced by the generator 270 passes through port 110-2 of the inertial filter 105 for optical analysis by analyzer 140.

Accordingly, the direction of the calibration gas through the inertial filter 105 is opposite in direction to a direction that the sample gas from the flue passes through the inertial filter 105.

Figure 6:
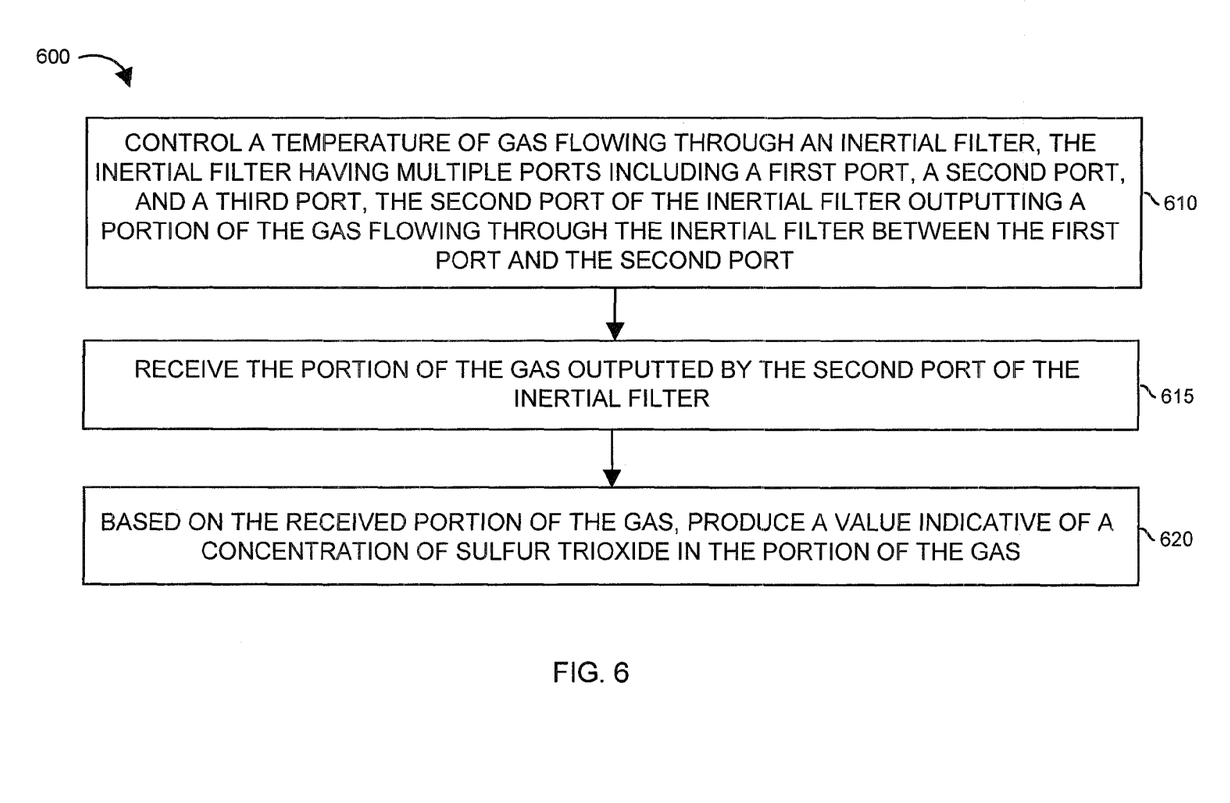
FIG. 6 is a flowchart illustrating an example method supporting generation of a value indicative of a concentration of sulfur trioxide in a sample gas according to embodiments herein.

FIG. 6 is a flowchart 600 illustrating a method of controlling environmental parameters for analyzing a gas sample according to embodiments herein. Note that there will be some overlap with respect to concepts discussed above for FIGS. 1 through 5.

In step 610, the temperature controller 130 controls a temperature of gas sample 115 flowing through the inertial filter 105. As previously discussed, the inertial filter 105 has multiple ports including port 110-1, port 110-2, and port 110-3. The port 110-2 of the inertial filter 105 outputs a portion of the gas sample flowing through the inertial filter 105 between the port 110-1 and the port 110-3.

In step 620, the conduit 120-2 receives the portion of the gas sample 115 outputted by port 110-2 of the inertial filter 105 and conveys the received portion of sample gas on a flow path towards the optical cavity 252 for further analysis by analyzer 140.

In step 630, based on the received portion of the gas sample 115 passing through the optical cavity 252, the analyzer 140 produces a value indicative of a concentration of sulfur trioxide in the gas sample 115.

Figure 7:
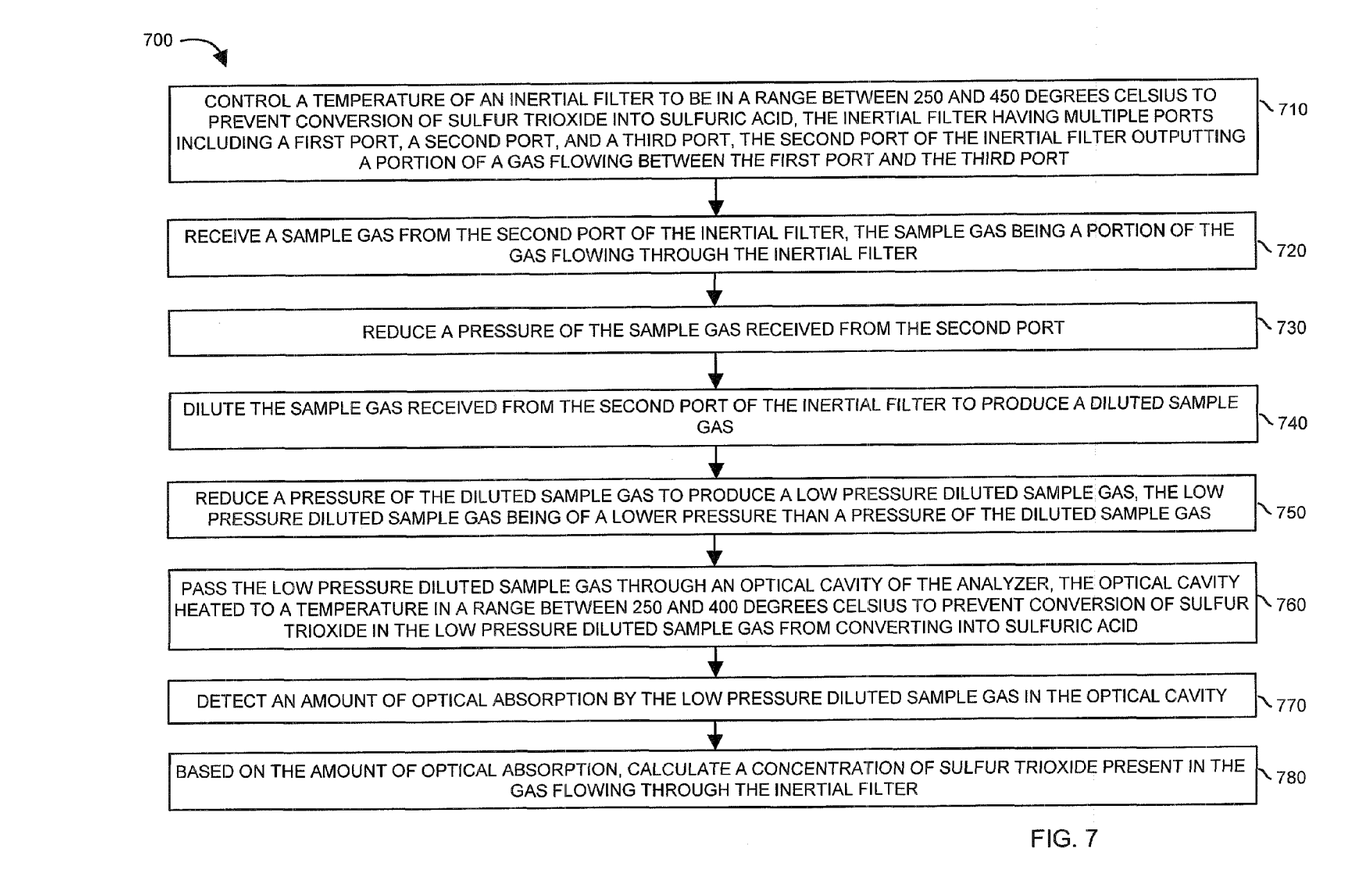
FIG. 7 is a flowchart illustrating an example method supporting generation of a value indicative of a concentration of sulfur trioxide in a sample gas according to embodiments herein.

FIG. 7 is a flowchart 700 illustrating a method of controlling environmental parameters for analyzing a gas sample according to embodiments herein. Note that there will be some overlap with respect to concepts discussed above.

In step 710, the temperature controller 130 controls a temperature of the inertial filter 105 to be in a range between 250 and 450 degrees Celsius to prevent conversion of sulfur trioxide into sulfuric acid.

In step 720, the conduit 120-2 receives a sample gas 115 from the port 110-2 of the inertial filter 105.

In step 730, the pressure reducer 220 reduces a pressure of the sample gas received from the port 110-2 of the inertial filter 105.

In step 740, the dilution module 230 dilutes the sample gas received from the port 110-2 of the inertial filter 105 to produce a diluted sample gas outputted to conduit 120-6.

In step 750, a combination of the outlet 243 and exhaust 265 reduces a pressure of the diluted sample gas (as outputted by the dilution module 230) to produce a low-pressure diluted sample gas. The low-pressure diluted sample gas passed through the optical cavity 252 has a lower pressure than a pressure of the diluted sample gas outputted by the dilution module 230.

In step 760, via the exhaust 265, the system 200 passes the low-pressure diluted sample gas through the optical cavity 252 associated with the analyzer 140. As previously discussed, in one embodiment, the optical cavity 252 is heated to a temperature in a range between 250 and 400 degrees Celsius to prevent conversion of sulfur trioxide in the low-pressure diluted sample gas passing through the optical cavity 252 from converting into sulfuric acid.

In step 770, the analyzer 140 detects an amount of optical absorption by the low-pressure diluted sample gas in the optical cavity 252.

In step 780, based on the amount of optical absorption by the gas sample passing through the optical cavity 252, the analyzer 140 calculates a concentration of sulfur trioxide present in the gas sample flowing through the inertial filter 105. In one embodiment, the analyzer 140 produces and displays a value indicative of a concentration of sulfur trioxide in the portion of the sample gas.

Figure 8:
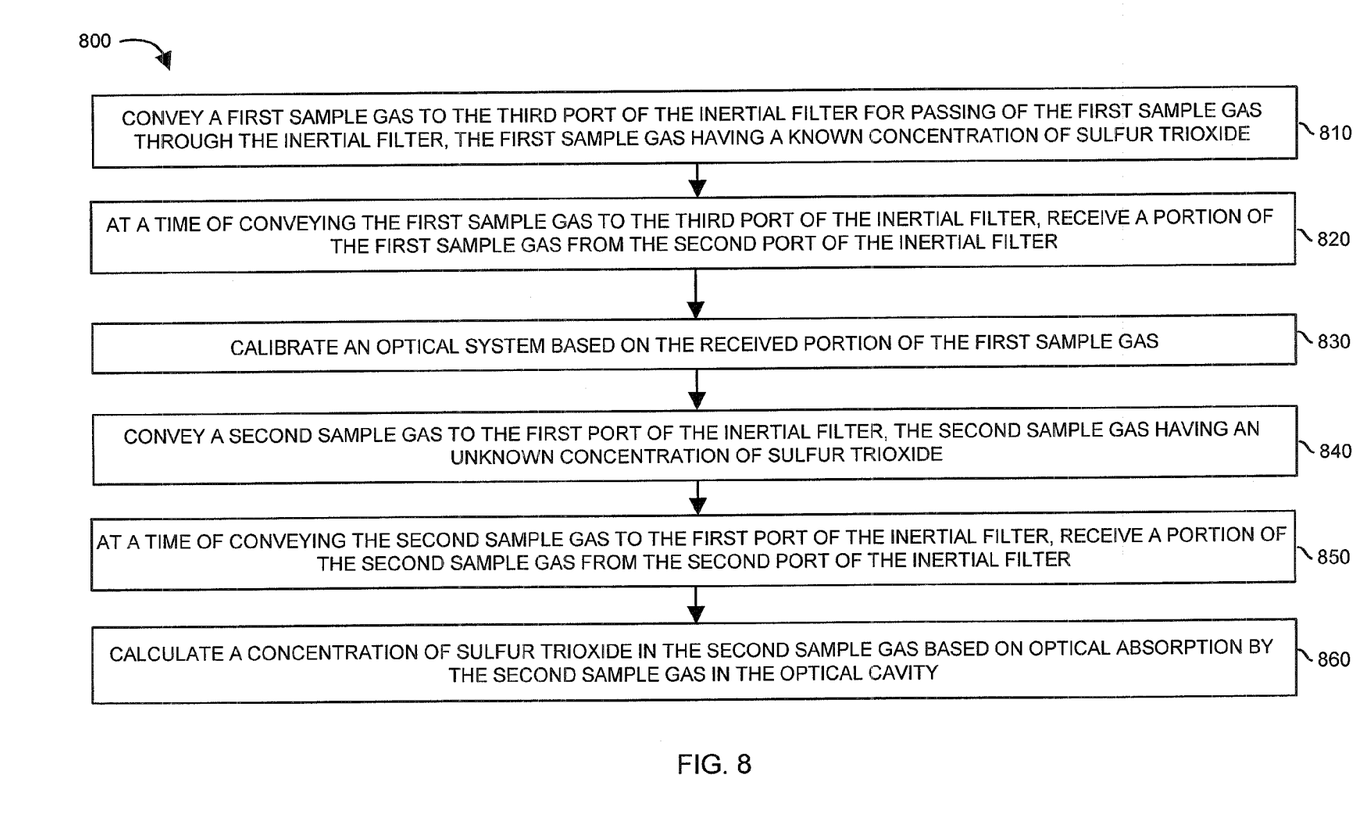
FIG. 8 is a flowchart illustrating an example method of utilizing an inertial filter according to embodiments herein.

FIG. 8 is a flowchart 800 illustrating a method of implementing flows of gases through an inertial filter according to embodiments herein.

In step 810, the system 200 conveys a first sample gas such as a calibration sample gas to port 110-3 of the inertial filter 105 for passing of the first sample gas through the inertial filter 105. The first sample gas has a known concentration of sulfur trioxide for calibrating analyzer 140 and related components.

In step 820, at a time of conveying the first sample gas to the third port of the inertial filter, conduit 120-2 receives a portion of the first sample gas from the second port of the inertial filter 105.

In step 830, the system 200 calibrates an optical system (e.g., a combination of optical cavity 252, optical source 250, detector 260, etc.) based on the received portion of the first sample gas.

In step 840, the system 200 conveys a second sample gas (e.g., from a source such as flue 211) to the first port 110-1 of the inertial filter 105. The second sample gas has an unknown concentration of sulfur trioxide and/or sulfuric acid.

In step 850, at a time of conveying the second sample gas to the port 110-1 of the inertial filter 105, the conduit 120-2 receives a portion of the second sample gas from the port 110-2 of the inertial filter 105.

In step 860, based on an amount optical absorption in the optical cavity 252, the analyzer 140 calculates a concentration of sulfur trioxide in the second sample gas.

Note again that techniques herein are well suited for use in detecting contaminants such as sulfur trioxide. However, it should be noted that embodiments herein are not limited to use in such applications and that the techniques discussed herein are suited for other applications as well.

Figure 9:
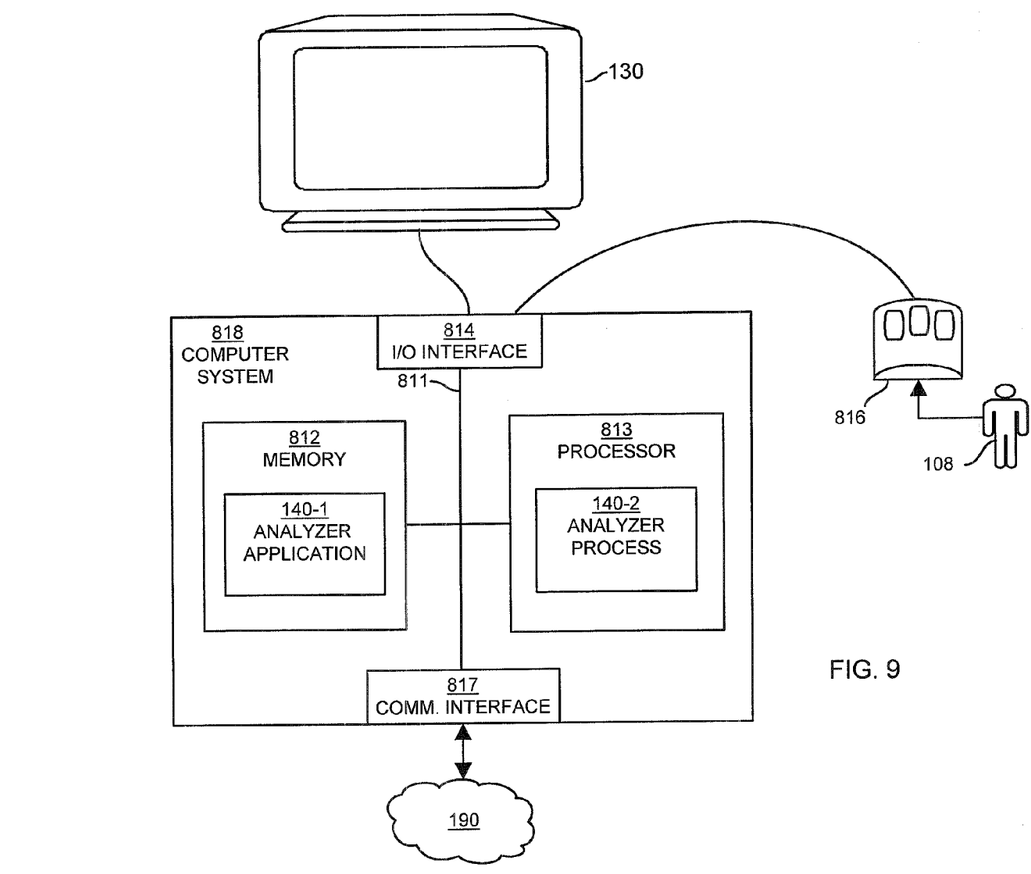
FIG. 9 is an example diagram illustrating a computer for executing software instructions to carry out operations according to embodiments herein.

FIG. 9 is a block diagram of an example architecture of a respective computer system 818 such as one or more computers, processes, etc., for implementing analyzer 140 and/or control of other environmental conditions according to embodiments herein. In other words, the analyzer 140 can include hardware and/or software that controls modules such as the temperature controller 130, dilution module 230, valves 210, flow controller 245, generator 270, exhaust 265, etc., to facilitate calibration and subsequent generation of concentration values as described herein.

Computer system 818 can include one or more computerized devices such as personal computers, workstations, portable computing devices, consoles, network terminals, networks, processing devices, etc.

Note that the following discussion provides a basic example embodiment indicating how to carry out all or portions of the functionality associated with the analyzer 140 as discussed above and below. However, it should be noted again that the actual configuration for carrying out the analyzer 140 can vary depending on a respective application. For example, as previously discussed, computer system 818 can include one or multiple computers that carry out the processing as described herein.

As shown, computer system 818 of the present example includes an interconnect 811 coupling memory system 812, a processor 813, I/O interface 814, and a communications interface 817.

I/O interface 814 provides connectivity to peripheral devices such as repository 180 and other devices 816 (if such devices are present) such as a keyboard, mouse (e.g., selection tool to move a cursor), display screen 130, etc.

Communications interface 817 enables the analyzer application 140-1 of computer system 818 to communicate over network 190 and, if necessary, retrieve data, update information, etc., from different sources.

As shown, memory system 812 can be encoded with instructions associated with analyzer application 140-1. The instructions support functionality as discussed above and as discussed further below. The analyzer application 140-1 (and/or other resources as described herein) can be embodied as software code such as data and/or logic instructions on a tangible and/or intangible computer readable medium, media, etc. such as memory or on another computer readable medium that supports processing functionality according to different embodiments described herein.

During operation of one embodiment, processor 813 accesses memory system 812 via the use of interconnect 811 in order to launch, run, execute, interpret or otherwise perform the logic instructions of the analyzer application 140-1. Execution of the analyzer application 140-1 produces processing functionality in analyzer process 140-2. In other words, the analyzer process 140-2 represents one or more portions of the analyzer 140 performing within or upon the processor 813 in the computer system 810.

It should be noted that, in addition to the analyzer process 140-2 that carries out method operations as discussed herein, other embodiments herein include the analyzer application 140-1 itself such as the un-executed or non-performing logic instructions and/or data, etc. The analyzer application 140-1 may be stored on a computer readable medium such as a floppy disk, hard disk or in an optical medium. According to other embodiments, the analyzer application 140-1 can also be stored in a memory type system such as in firmware, read only memory (ROM), or, as in this example, as executable code within the memory system 812 (e.g., within Random Access Memory or RAM).

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. A system comprising:
an inertial filter having multiple ports including a first port, a second port, and a third port, the second port of the inertial filter outputting a portion of a gas flowing between the first port and the third port;
a temperature controller configured to control a temperature of the gas flowing in the inertial filter;
an analyzer configured to receive the portion of the gas flow from the second port of the inertial filter and produce a value indicative of a concentration of sulfur trioxide in the portion of the gas flow; and
wherein the temperature controller controls the inertial filter to a temperature in a range between 250 and 450 degrees Celsius to prevent conversion of sulfur trioxide in the portion of the gas from converting into sulfuric acid.

2. The system as in claim 1, wherein the analyzer includes an optical cavity through which to pass a sample gas received from the second port of the inertial filter, the analyzer detecting a concentration of sulfur trioxide in the sample gas received from the second port based on an amount of optical absorption by the sample gas in the optical cavity.

3. The system as in claim 2, wherein the optical cavity is heated to a temperature in a range between 250 and 400 degrees Celsius.

4. The system as in claim 1 further comprising:
a dilution module configured to produce a diluted sample gas based on dilution of the portion of gas received from the second port of the inertial filter, the analyzer detecting a concentration of sulfur trioxide in the diluted sample gas based on an amount of optical absorption by the diluted sample gas.

5. The system as in claim 4 further comprising:
a pressure reducer configured to reduce a pressure of the sample gas received from the second port prior to dilution of the sample gas by the dilution module.

6. The system as in claim 5, wherein the pressure reducer is configured to reduce a pressure of the diluted sample gas produced by the dilution module prior to passing of the diluted sample gas through an optical cavity of the analyzer, the analyzer measuring an amount of absorption resulting from presence of the diluted sample gas in the optical cavity.

7. The system as in claim 6 further comprising:
a heater configured to heat the optical cavity to prevent conversion of sulfur trioxide in the diluted sample gas into sulfuric acid.

8. The system as in claim 1 further comprising:
a first conduit, the first conduit conveying a first sample gas to the first port of the inertial filter, the first sample gas having an unknown concentration of sulfur trioxide; and
a second conduit, the second conduit conveying a second sample gas to the third port of the inertial filter, the second sample gas having a known concentration of sulfur trioxide.

9. The system as in claim 8, wherein the second conduit conveys, during a first duration of time, the second sample gas from a gas generator source to the third port of the inertial filter, a portion of the second sample gas outputted from the second port of the inertial filter being used to calibrate an optical absorption cavity associated with the analyzer; and
wherein the first conduit conveys, during a second duration of time, the first sample gas from a flue source to the first port of the inertial filter, a portion of the first sample gas outputted by the second port of the inertial filter to the optical cavity being used to determine an optical absorption value associated with the first sample gas, the analyzer utilizing the optical absorption value to calculate a concentration of sulfur trioxide in the first sample gas.

10. A method comprising:
controlling a temperature of gas flowing through an inertial filter, the inertial filter having multiple ports including a first port, a second port, and a third port, the second port of the inertial filter outputting a portion of a gas flowing between the first port and the third port;
receiving the portion of the gas flow from the second port of the inertial filter;
based on the received portion of the gas flow, producing a value indicative of a concentration of sulfur trioxide in the portion of the gas flow; and
wherein controlling the temperature includes: controlling the inertial filter to be a temperature in a range between 250 and 450 degrees Celsius to prevent conversion of sulfur trioxide in the received portion of the gas from converting into sulfuric acid.

11. The method as in claim 10 further comprising:
detecting a concentration of sulfur trioxide in sample gas received from the second port of the inertial filter based on an amount of optical absorption by the sample gas in the optical cavity.

12. The method as in claim 11 further comprising:
heating the optical cavity to a temperature in a range between 250 and 400 degrees Celsius to prevent conversion of sulfur trioxide in the received portion of the gas from converting into sulfuric acid.

13. The method as in claim 10 further comprising:
diluting the portion of gas received from the second port of the inertial filter to produce a diluted sample gas; and
detecting a concentration of sulfur trioxide in the diluted sample gas based on an amount of optical absorption by the diluted sample gas.

14. The method as in claim 13 further comprising:
reducing a pressure of the sample gas received from the second port prior to producing the diluted sample gas.

15. The method as in claim 14 further comprising:
reducing a pressure of the diluted sample gas to produce a low pressure diluted sample gas;
passing the low pressure diluted sample gas through an optical cavity of the analyzer; and
based on optical absorption by the low pressure diluted sample gas in the optical cavity, calculating a concentration of sulfur trioxide present in the gas flowing between the first port and second port of the inertial filter.

16. The method as in claim 15 further comprising:

heating the optical cavity to prevent conversion of sulfur trioxide in the diluted sample gas into sulfuric acid.

17. The method as in claim 10 further comprising:

conveying a first sample gas to the third port of the inertial filter, the first sample gas having a known concentration of sulfur trioxide; and conveying a second sample gas to the first port of the inertial filter, the second sample gas having an unknown concentration of sulfur trioxide.

18. The method as in claim 17 further comprising:

at a time of conveying the first sample gas to the third port of the inertial filter, receiving a portion of the first sample gas from the second port of the inertial filter;

calibrating an optical system based on the received portion of the first sample gas;

at a time of conveying the second sample gas to the first port of the inertial filter, receiving a portion of the second sample gas from the second port of the inertial filter; and calculating a concentration of sulfur trioxide in the second sample gas based on optical absorption by the second sample gas in the optical system.

19. The system as in claim 1, wherein the temperature controller increases the temperature of the gas to drive sulfuric acid in the gas to sulfur trioxide.

20. The system as in claim 1, wherein the temperature controller decreases the temperature of the gas to drive the sulfur trioxide in the gas to sulfuric acid.

* * * * *